United States Patent [19]

Leroy et al.

[11] 4,211,795

[45] * Jul. 8, 1980

[54] ANIMAL FEEDS

[75] Inventors: Francoise A. J. Leroy, St. Leu la Foret; Zelmen Zelter; Andre' C. Francois, both of Paris; Andre' Chassin, Saint-Junien; Jacques Rodeaud, Chabanais, all of France

[73] Assignee: Institut National de la Recherche Agronomique and Aussedat-Rey, Paris, France

[ * ] Notice: The portion of the term of this patent subsequent to Apr. 21, 1987, has been disclaimed.

[21] Appl. No.: 532,153

[22] Filed: Dec. 24, 1974

Related U.S. Application Data

[63] Continuation-in-part of Ser. No. 845,902, Jul. 29, 1969, and Ser. No. 524,837, Feb. 3, 1966, Pat. No. 3,507,662.

[30] Foreign Application Priority Data

Feb. 3, 1965 [FR] France .................................. 65.4208
Feb. 3, 1965 [FR] France .................................. 65.4787

[51] Int. Cl.² .......................... A23K 1/04; A23K 1/14
[52] U.S. Cl. ....................................... 426/2; 426/635; 426/647; 426/656; 426/807; 260/112 R; 260/119

[58] Field of Search ................. 260/473.5, 473.6, 566, 260/601, 521, 112, 119, 123.5; 424/177; 71/28, 30; 426/2, 69, 71, 89, 92, 93, 96, 98, 289, 302, 615, 623, 630, 635, 656, 657, 807

[56] References Cited

U.S. PATENT DOCUMENTS

| | | | |
|---|---|---|---|
| 1,841,797 | 1/1932 | Ernst et al. | 260/117 |
| 2,951,761 | 9/1960 | Stephan | 99/3 |
| 3,356,518 | 12/1967 | Gilboe | 260/123.5 |
| 3,507,662 | 4/1970 | Leroy et al. | 426/807 |
| 3,619,200 | 11/1971 | Ferguson et al. | 426/807 |
| 3,925,560 | 12/1975 | Scott | 426/807 |
| 3,966,998 | 6/1976 | Rawlings | 426/634 |

OTHER PUBLICATIONS

Feeds and Feeding, Morrison 22nd Ed., Morrison Pub. Co., 1957, Ithaca, N. Y., pp. 21, 22.

*Primary Examiner*—Hiram H. Bernstein
*Attorney, Agent, or Firm*—Oblon, Fisher, Spivak, McClelland & Maier

[57] ABSTRACT

A nitrogenous animal feed complex and especially a proteinaceous animal feed complex, comprising a protein organic tanning substance complex that protects the proteinaceous feed against bacterial deamination in the upper regions of the alimentary tract (typically in the rumen of a ruminant), and dissociates in the presence of the proteolytic enzymes present in the lower regions of the alimentary tract.

7 Claims, 4 Drawing Figures

TANNING WITH: A TANNING EXTRACT OF CHESTNUT (CHES); QUEBRACHO (QUE)

●——● CELLULOSE DEGRADATION ACTIVITY OF RUMEN FLUID
●----● "IN VITRO" PROTEIN DEAMINATION

1

ANIMAL FEEDS

CROSS-REFERENCES TO RELATED APPLICATIONS

This application is a continuation-in-part of application Ser. No. 845,902, filed July 29, 1969, and application Ser. No. 524,837, filed Feb. 3, 1966, which is now U.S. Pat. No. 3,507,662.

BACKGROUND OF THE INVENTION

1. Field of Invention

This invention pertains to the complete avoidance, or substantial diminution, of the deamination of proteins and like amino or amide compounds in the upper regions of the alimentary tracts of polygastric animals, such as ruminants, while preserving the capacity of such animal feeds to be assimilated in lower regions of the alimentary tract, such as in the intestines. This objective is obtained by providing an animal feed containing as an essential component a nitrogenous animal feed-tanning agent complex; customarily a proteinous animal feed-tanning agent complex.

2. Description of Prior Art

The use of tannins in animal feeding has already been proposed. Certain documents illustrating the prior art will be cited below.

U.S. Pat. No. 2,564,106, filed on Oct. 29, 1948, and granted on Aug. 14, 1951, relates to antioxidant mixtures intended to be incorporated into animal feeds, consisting essentially of synergistic mixtures of beta-substituted mercaptopropionic acids with antioxidant compounds, among which the tannins are mentioned. For the very special purpose which is the object of this disclosure, the antioxidant mixture is used in very small amounts, not greater than 1% by weight.

French Pat. No. 1,110,038, filed Oct. 14, 1954, and granted Oct. 5, 1955, also concerns complex antioxidant preparations for the treatment of food substances intended for animals. In these preparations it is possible to use substances capable of blocking mineral elements in a complex state, inactive on the oxidizability of lipids, such as phosphates or tannins.

French Pat. No. 1,261,199, filed Jan. 7, 1960, and granted on Apr. 10, 1961, describes complete compound animal feeds. It provides for the use in these feeds of substances to encourage appetite, such as tannins, gentian, cinchoan, etc.

GENERAL DESCRIPTION OF THE INVENTION

The present invention relates to nitrogenous animal feeds and more particularly to proteinaceous animal feeds and especially feedstuff for ruminant or other polygastric animals, of plant, animal or synthetic origin. More particularly, the invention relates to a process for preparing with tanning agents, nitrogenous and especially proteinous feeds which, otherwise, would be liable to be partially or wholly degraded into ammonia by the digestive flora present in the upper compartments of the alimentary tract before reaching the portion where proteins are hydrolyzed by proteolytic enzymes (pepsin, trypsin ...) for absorption by a polygastric animal in the form of amino acids. Protein digestion occurs in the abomasum and the small intestine of polygastric animals or ruminant animals.

Figure 1A:
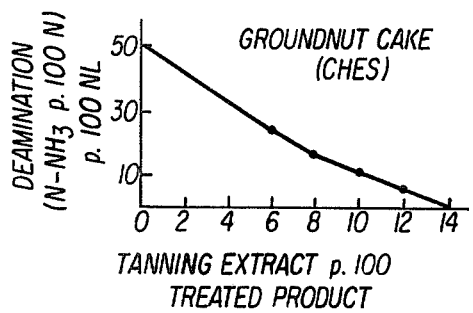
FIG. 1. A through H, is an assemblage of eight graphs illustrating the effect of treatment of proteins with chestnut tanin and quebracho tannin on microbial degradation in the rumen.
Figure 1B:
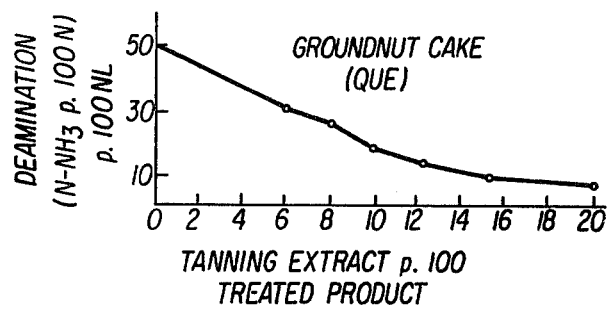
Figure 1C:
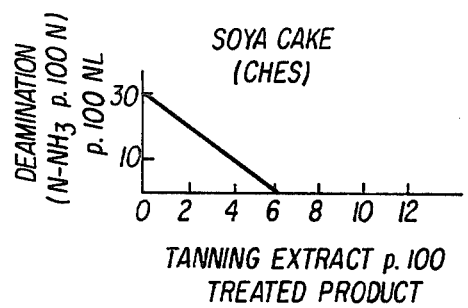
Figure 1D:
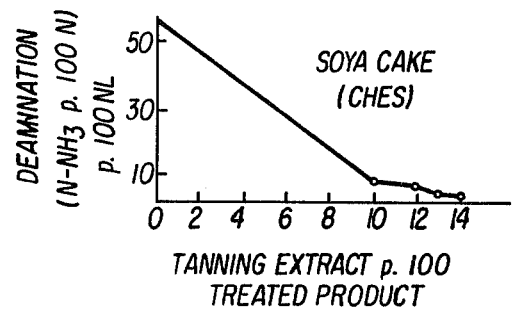
Figure 1E:
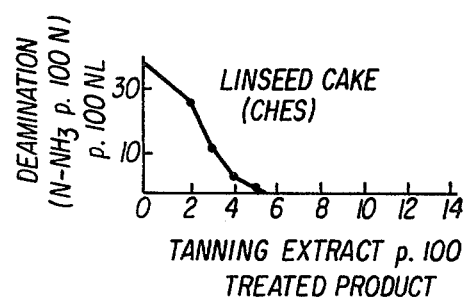
Figure 1F:
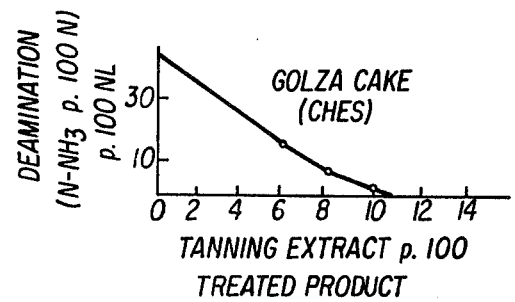
Figure 1G:
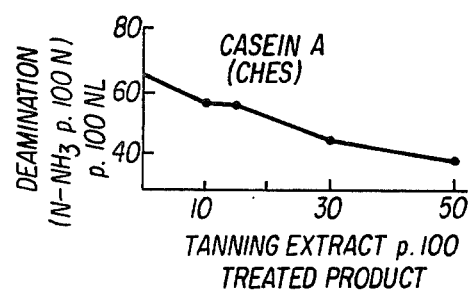
Figure 1H:
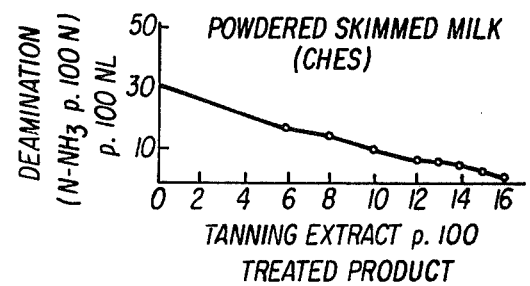
Figure 2A:
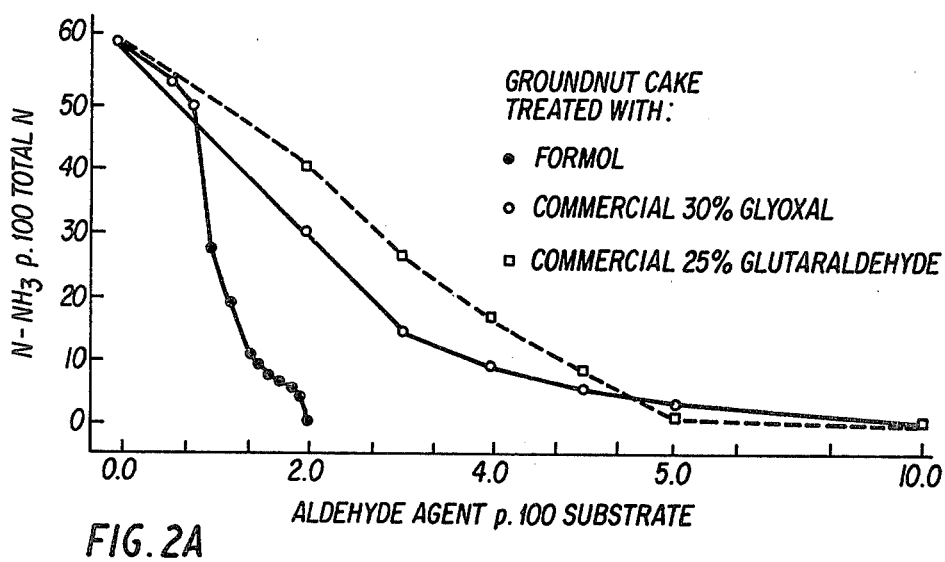
FIG. 2. A through D, illustrates the effect of the dose of an aldehyde on the deamination of protein in "in vitro" rumen medium.
Figure 2B:
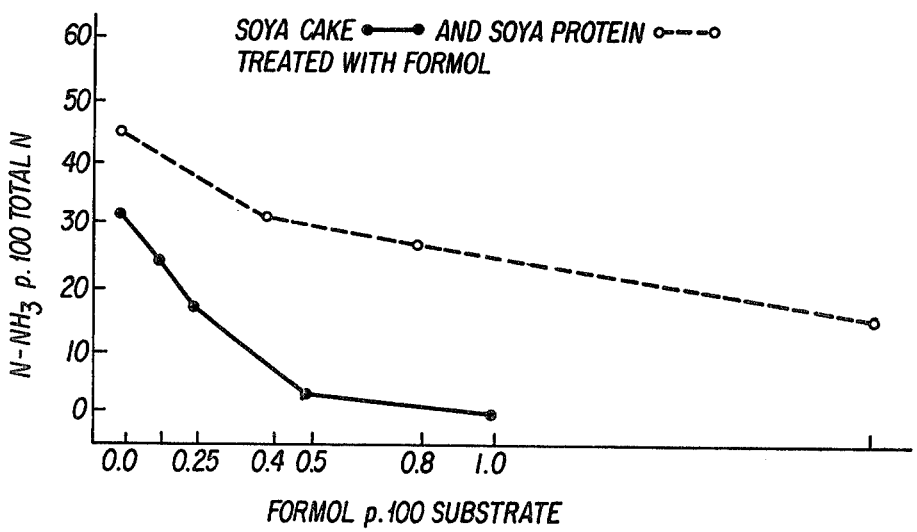
Figure 2C:
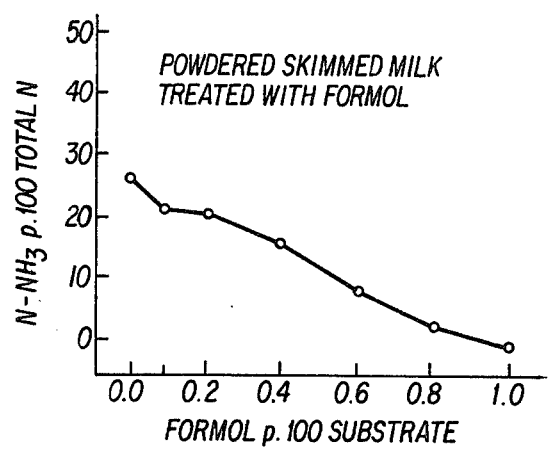
Figure 2D:
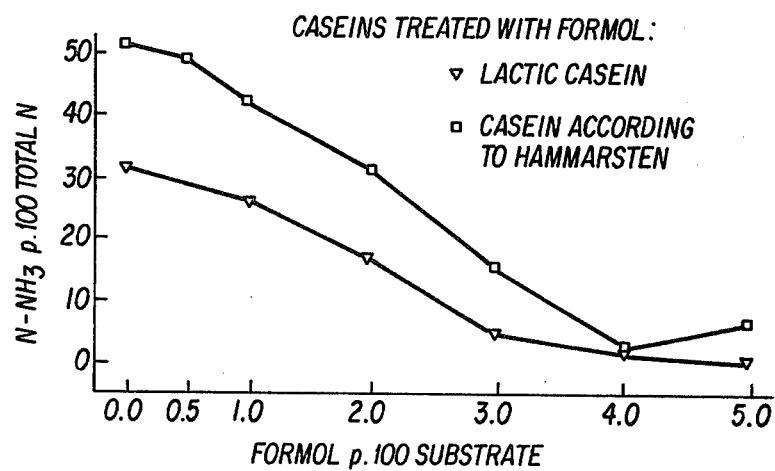

The drawings are more fully explained below.

MORE DETAILED DESCRIPTION OF THE INVENTION

In the present description, the term "nitrogenous feeds" or "proteinous feeds" refers to soluble and insoluble, native and denatured proteins and polypeptides.

Among the nitrogenous feeds (especially proteinous feeds) for consumption by animals, and suitable for use in the process of the invention may be mentioned: oil-seed cakes, fodder plant and cereal animal meals, nitrogenous materials extracted from milk or eggs, fungal or bacterial nitrogenous materials, products which can be used for feeding animals and apt to be degraded by the microorganisms in the alimentary tract more especially into ammonia. The following may also be used: powdered milk, lactic casein, fish meal (tunny, sardine, whale, herring, etc.) fowl feather meal, soluble fish, fowl giblet meal, fish hydrolysates and autolysates, blood meal, meat, various gelatines, dried lactalbumines, skimmed milk, fodder plant meals, groundnut, linseed, colza or rape, poppy-seed, palm cabbage, sesame, soya and sunflower seed cake, yeasts and microorganisms and maize gluten, etc.

The invention provides means for protecting such feeds from microbial or bacterial degradation in the portion of the alimentary tract of animals before the portion where the proteolytic enzymes (pepsin, trypsin, etc.), are secreted without detriment to the digestive action of the proteolytic enzymes. This improves the utilization of the protein for maintenance, growth or lactation.

This degradation, which is detrimental to the nutritive efficiency of such feeds, is especially manifest in ruminants and in general in all polygastric animals, due to the presence in one of their stomach cavities, the rumen, of an abundant and very active deaminating microflora, living there in symbiosis with the host. The bacterial micropopulation cause a greater or lesser degree of deamination of proteins. It then becomes impossible for said bacteria to use the total amount of ammonia formed by their own activity for the synthesis of microbial proteins digested in the ulterior compartments of the alimentary tract. A variable fraction, which may be more than two thirds of this amount of ammonia, is eliminated in the urine, consequently causing a loss of alimentary nitrogen which may be as great as 40 to 80% according to the type of nitrogenous feed. Such a loss is obviously prejudicial to the effectiveness of the protein feeds, that is to say, to the growth and production of animals. Furthermore, the microbial protein formed from the ammonia in the rumen does not contain all the essential amino acids in the relative amounts that may be supplied in the original feed for maximum protein production by the ruminant.

It is known that the bacterial deamination faculty of nitrogenous feeds is closely connected with their physiochemical properties and especially to their degree of solubility. The most striking examples are casein which is completely soluble and is almost totally degraded and, on the contrary, dry distillery yeasts whose absolutely insoluble nitrogen does not generate any notable amount of ammonia in the ruminant's paunch.

Nevertheless, products insoluble in buffer media, similar to those of the rumen, can be significantly degraded into ammonia. It is therefore impossible to assess the quality of a protective treatment starting simply with the physical criterion of solubility. For this reason, the only criterion retained in the invention for assessing the quality of the treatment is the degradation of nitrogenous material into ammonia in a rumen medium.

A correctly treated product will result in significantly lower level of ammonia production, when compared with the untreated product.

Degradation of the protein and the efficiency of the protective treatment are determined by the "in vitro" rumen method. Said method is derived from the techniques used by TISSERAND and ZELTER (standarization trials on a technique for measuring the in vitro degradation of fodder in an artificial rumen "Ann. Biol. Anim. Bioch. Biophys." 1965 5 (1) 101–111). It necessitates an inoculum taken from sheep having a permanent rumen fistula. The sheep are previously adapted to the substance studied, or to a diet of concentrate and hay.

The test protein is incubated anaerobically in duplicate at 39° C. for 16 hours in the presence of a mixture of artificial saliva and inoculum or rumen liquor filtered through gauze. The incubation medium is stirred by a slow $CO_2$ bubble by bubble process. After incubation has been stopped, the ammonia present in the rumen medium is determined by any known appropriate method.

A blank control is obtained by replacing the protein studied by an equal weight of straw.

CALCULATIONS

Generally, two ways are used to present evaluative results:

Deamination, which permits substances of different natures to be compared, is expressed as $N-NH_3$ appearing as a % of initial N. It is calculated by the following formula:

$$\text{Deamination \%} = 100 \times \frac{(N-NH_3 \text{ of the rumen containing protein}) - (N-NH_3 \text{ of the rumen containing straw})}{\text{Protein N put to incubate}}$$

(as % total N)
($N-NH_3$ means the amount of N deaminated expressed in terms of $NH_3$)

Deamination base 100 is used to study the decrease in protein degradation induced by the protective treatment.

$$\text{Deamination base 100} = 100 \times \frac{\text{Deamination of the treated protein}}{\text{Deamination of the same protein untreated}}$$

The "in vitro" deamination test in "artificial rumen" is the only criterion retained to assess the quality of the protective treatment defined in this disclosure. It should, however, be noted that the products obtained by the "tanning" process should meet the following other nutritional criteria:

(1) The proteins treated should be hydrolysable by the proteolytic enzymes of the alimentary tract (pepsin, trypsin, chymotrypsin, carboxy peptidases, etc.). Conventional peptic solubility test will enable one to determine the availability of said proteins to the animal to be checked.

(2) The treatment of proteins should not reduce the indispensable metabolic activities of the ruminal micropopulation. This can be verified by taking as a criterion a cellulose degradation in rumen test, derived from the "in vitro" rumen test mentioned hereinabove.

For nutritional reasons, or taking technological or economic considerations into account, it is possible to permit only an uncomplete protection and allow part of the protein to be affected by microbial degradation, provided, of course, that the degree of protection is substantial, i.e. truly significant.

Hardening of proteins by very intensive thermal treatment provides only very insufficient protection against deamination; furthermore, it has the very serious drawbacks of making proteins more indigestible, and causing destruction and a notable reduction of the biological availability of essential amino acids.

In the prior art products, the presence of free tannins or of natural complexes, which we know alters the susceptibility of the protein to bacterial action, appreciably impairs its reaction to the proteolytic enzymes in the digestive tract. The invention differs from there prior art products in that these new complexes can be destroyed in the lower portion of the digestive tract, without the harmful effect of the free tannin being discernable, owing to the fact of its being freed progressively with simultaneous destruction or inactivation of the tannin compound. In this invention, hydrolyzable tannins (gallotannins and ellagitannins) as well as some synthetic organic tannins (aldehydes) answer this criterion very closely.

The present invention makes use of the property possessed by natural or synthetic tanning substances to render water soluble proteins insoluble and to increase their resistance to microbial or bacterial attack. The highly astringent tannins are those which posses the greatest affinity for proteins.

Natural substances possessing the power of tanning are polyphenols, of very varied nature and composition. They are classified into two main groups which, though they both include polyphenolic acids, are distinguished by their aptitude to be hydrolyzed into their simple components. These two groups are:

-condensed or catechic tannins which are not hydrolyzable by enzymes (tannase, emulsine . . . ) into their components and provide pyrocatechol on dry distillation.

-hydrolyzable tannins, degraded by hydrolyzing enzymes and their components, are esters of hexoses and phenol carbonic acids such as tannic acid, gallic acid, ellagic acid (ellegitannins); the ellagitannins are sometimes classified in a separate group.

Synthetic tanning substances having at least the aldehyde chemical function may be mentioned: formaldehyde, glyoxal, glutaraldehyde, acroleine (as examples).

Such short chain aldehydes are the preferred synthetic tanning substances.

The essential object of the invention, therefore, is to protect the nitrogenous feeds from bacterial degradation, avoiding the serious drawbacks inherent to intensive heat treatment. It renders nitrogenous feeds resistant to attack by bacteria in the rumen, but in such a way as to leave them completely accessible to the indispensable action of proteolytic enzymes which occur in the ulterior compartments of the alimentary tract. The treatment advocated in no way disturbs the no less essential activity of the cellulolytic bacteria of the rumen, whose role in the assimilation of glucide foods, especially fodders, is of prime importance for ruminants.

Generally speaking, the process of the invention is used for preparing nitrogenous feeds for polygastric animals, and more especially for ruminants, with a view to protecting said feeds from microbial deamination.

All tanning substances of natural or synthetic origin which have the property of stabilizing proteins in the state of complexes by means of a suitable treatment, described below can be used in this invention provided the proteins protected from the deaminating action of the microorganisms in the rumen remain dissociable by proteolytic enzymes of the alimentary tract.

The theoretical nature of the combination of tanning substances and proteins is not well understood and varies with the nature of the tanning substance. While in no way limiting the scope of the invention by theoretical explanations, it may be assumed that the tanning agents form "bridges" between the macromolecules constituting the proteins. This results in an overall increase of the molecular weight, rendering solvatation more difficult, increasing stability of the proteins and reducing their degradation by microorganisms into ammonia. The chemical nature of the intermolecular bridges is not clearly defined. Hydrogen type bonds, covalent bonds and ionic bonds occur. Depending upon the chemical nature of the tanning substance, the nature of the protein and the conditions of treatment, certain types of bonds can be the most important. Thus, in the case of tannin of plant origin, it is thought that the hydrogen type bond between phenolic functions existing in plant tannins and the keto imide group of the peptide linkages of proteins plays an especially important part.

Quinones react rapidly with proteins to form covalent bonds. The bond formed between phenols and substituted N amides, particularly the peptide CO—NH bond, is a hydrogen bond of the strongest type. In the case of condensed tannins, this bond occurs between phenol groups and the substituted amide groups of the protein. In the case of hydrolyzable tannins, these strong hydrogen bonds are formed with the carboxyl groups of tannins, and the weaker hydrogen bonds are formed with the hydroxyl groups of phenols.

To sum it up, and simplify it, we believe that the natural tannin-protein bond existing under the tanning conditions we use can be defined by a bond of the hydrogen type involving mainly the peptide bonds of the protein and the OH groups of the tannin.

With aldehydes, the nature of the bonds between the tanning substance and the protein is considered to be different. In the case of formol, for example, there is addition on the free amino groups and the creation of bonds between proteidic chains. Said bond, after the initial addition on the amino group, can form a methylene "bridge" with the phenolic or imidazole groups. This type of bond, notably with the $\epsilon$ amino group of lysine can have important nutritional consequences.

The invention has shown that several factors play a critical part in the manufacture of the nitrogenous feed with the tanning substance.

The nature of the tanning substance affects the amount of tanning agent necessary to provide good protection of the protein. Thus, with a groundnut cake treated under the same conditions, it is easy to ascertain that the dose enabling complete protection to be obtained varies considerably with the nature of the tanning substance. This dose is 19% with Quebracho tannin, 15% with chestnut tannin, 6% with a commercial 30% glyoxal solution, 6% with a commercial 30% glutaraldehyde solution and 2% with a commerical 30% formaldehyde solution. Allowing for plant tannin extract containing about 70% active ingredient, we can conclude that formol is 22 times more effective than Quebracho tannin.

Furthermore, the protective effect of tanning substances of different chemical characteristics appears to be additive. Thus, groundnut cakes can also be protected by the association of 7.5% chestnut tannin and 1.0% of a commercial 30% formol solution—or half the effective dose, when said tanning agents are used alone to protect said cake.

The nature of the feed substrate to be protected also has an effect on the dose of the tanning agent necessary to ensure sufficient protection. Thus, for examle, when processing under the same conditions with formol, it was found that complete protection could be obtained with the following doses of commercial 30% formol solution: 4% for casein and soya protein, 2% for groundnut cake, 1.4% for colza cake and 1% for soya cake.

The requisite condition is that the dose of tanning substance used should not be toxic and should be sufficient to block at least the major portion and preferably the quasi-total of the amino and amide groups to be protected in the proteinaceous feed.

The technical means to be used to carry out the treatment varies with the nature of the tanning agent used, the nature of the protein to be treated and the industrial equipment available. Without wishing to limit the characteristics of the apparatus necessary by definitions which are too precise, it may be said that it should permit the protein and tanning substance to be intimately contacted, and must ensure that the tanning substance (which is generally present in very small amounts compared with the protein) is dispersed in the most homogenous manner possible throughout the mass.

Taking the preceding fact into account, the feed treatment could be applied in very varied media. It could be made in a relatively high moisture medium, with the formation of a homogenous paste, followed by drying at moderate temperature. In a high moisture medium, it will sometimes be advantageous to modify the pH to promote the reaction velocity or to add substances encouraging precipitation of proteins (salts for example). But it can also be effected in a comparatively dry medium (7 to 13% moisture content for example), as the tanned product can be kept under these conditions without subsequent drying being necessary. The treatment can also be made in an organic solvent media, such as hexane, acetone, ether or alcohol, or in vapour phase (with gaseous formol for example). The time necessary for the protein and tanning substance to remain in contact to obtain suitable protection varies with the type of treatment: maximum protection can be attained in a few hours in some cases, but it can also require several weeks in others. Among the parameters which affect the speed at which protection is obtained the following may be mentioned in a non-limiting manner: temperature of the medium, amount of water, nature of the tanning substance, homogeneity of incorporation of the tanning agent into the mass and the extent to which intimate contact between protein and the tanning substance is obtained.

The protective treatment results in a significant decrease in the production of ammonia from the protein. However, protein protected by our process under correct technological conditions remains hydrolyzable by the proteolytic enzymes of the alimentary tract (pepsin for example) and available to the animal.

These results may appear contrary to the prior work on products containing tannin: certain types of tannins have a negative effect on the efficiency of proteins.

For instance, S. I. Chane, H. I. FULLER (Poultry Science, 1964, 43, 1, 30–36, "Effect of tannin acid content of grain sorghum on their feeding value for growing chicks") have shown that in monogastric animals, sorghum tannin prevents digestibility of the protein of these grains. These authors found that the higher the tanning content of the sorghum, the lower is their utilization by growing fowls.

Huisman, (Thesis 1946, Wageningen University quoted by E. Brouwer "Some observations in Holland on protein materials in the feeding of domestic animals"(Ed. Desoer-Liege, Beegium 2499)) has shown that in the case of guinea pigs, the greater the amount of tannic acid added to the ration, the less digestible the nitrogenous materials became. For instance, a value of 57.9% digestibility was found for a tannic acid level equal to 0%, of 40.6% for a level of 2.5% and 36.7% for a level of 5%.

C. Charlet-lery, A. M. Leroy, S. Z. ZELTER (Annales de Zootechnie 1955, 4,321–322. "Research into the alimentary effectiveness of farm apple residue V. Study on the apparent digestibility for sheep and pigs of the constituents of fresh, ensiled or dehydrated apple residue) have shown that, for ruminants and monogastric animals, the nitrogenous fraction of apples residue is indigestible, owing to its high tannin content, especially for ruminants and pigs.

Oslage H. J. Becker M. (Arch. Tierernahrung, 1958, 8,271–277 Verusche über dem Nahrwert von Johannisbrot beim Wiederkauer insbesondere über die Beeintrachtigung der Eiweissverdaulichkeit durch die Gerbsaüre des Futtermittels) have shown that in the case of ruminants, carob proteins are indigestible owing to the presence of tannic acid.

These various prior studies show that if tannins are used in animal feeding without special precautions being taken in the manner they are combined with the feed, results may be obtained which are injurious to the animals' system. The process of the invention provides a strictly controlled method for tanning the proteins of an animal feed intended for ruminants, without risks of toxicity, and in a way that effectively protects the proteins from microbial degradation and prevents the formation of non-digestible feed-tannin products.

When the feed-tannin complex of this invention is formed in an aqueous paste reaction medium, the paste should not exude any liquid. The paste is left to react until analysis shows that there is practically no remaining soluble protein. Then, the product is dried, preferably at a temperature not higher than 80° C.

Commercial tanning substances which can be used in the process of the invention are essentially of plant vegetable origin : bark, wood, roots, trunks, leaves, etc. of chestnut, oak, myrobalan, valonia, quebracho, mimosa, eucalyptus. Among native woods, oak and chestnut are usually used for making tannin.

The tannic extract of chestnut wood belongs to the group of pyrogallic tannins, more especially to that of the ellagitannins. It contains free gallic acid, free ellagic acid and polyphenol compounds (of not clearly defined structure) which are probably hexoses derived from gallic acid.

After hydrolysis it gives gallic acid, ellagic acid and hexoses (about 10%), about half of which is glucose.

An extract such as this can be obtained from chips which are submitted to methodical extraction by hot water, at about 80° C. for instance, after which the extract may be concentrated in vacuum to obtain a paste which is dried and which provides a fine powder.

All commercial forms of tannin are suitable for use in the invention, but it should be noted that the process described may use all other natural or synthetic tanning substances which, like chestnut tannin, possess the property of forming complexes with edible proteins which resist bacterial deamination but are dissociable by the proteolytic enzymes of the alimentary tract without inhibiting the bacterial cellulolytic activity in the ruminant's paunch.

Our discoveries have shown that several factors play a critical part in the elaboration of the nitrogenous feeds with the tanning substance.

The first factor is the quantity of tanning substance used. The requisite condition is that the dose or amount of tannin used should not be toxic when complexed and should be sufficient to block at least the major portion and preferably all portion of the amino and amide groups to be protected in the proteinaceous feed. In general, our discoveries have shown, for instance, that the tanning substance should normally be incorporated in an amount of 0.5 to 20% by weight of the feed (which may include nitrogen free components such as glucides, fats, minerals, etc.) or 1 to 40% based on the nitrogenous feed fraction alone. The preferred rage generally being between 6 and 15% when vegetable tannin is used and 1 to 10% when aldehyde tannins are used. At levels lower than these for instance, the desired results, that is to say, the complete protection of proteins against bacterial deamination is not obtained. In general from 15% upwards the results obtained are not economically better than for values of between 6 and 15%.

A second essential factor which should be taken into account in the paste reaction process of the invention is the amount of water incorporated in the dry mass of nitrogenous feed, that is to say, in the mixture of crude protein and tanning substance. When a protein is treated, there should be a sufficient amount of water to allow subsequent swelling of the proteins, but it should not be in excess with respect to this amount. In general an amount of water in the range of 2.5 to 3 times the weight of the nitrogenous feed to be treated answers the purpose. The choice of temperature of the water incorporated is also important. Of course, an excess of water can be used and centrifuged off, for instance, with a consequent loss of water soluble constituents.

All excess water which is not absorbed by the mixture might exude and cause losses of soluble nutrients and tanning agents. Water at a temperature of up to 60° to 70° C. may be used, but the results are no more satisfactory than when water at a normal temperature is used. Therefore it is preferable, for obvious economical reasons, to use water at the ordinary temperature. On the other hand, water heated to 95°–100° C. before being incorporated with the dry mixture of the tanning substance and the proteinaceous feed causes lumping phenomena. The particles of proteinaceous feeds embedded inside these lumps therefore mostly escape tanning and they are thus not adequately protected from bacterial degradation.

It should, moreover, be noted that it is often preferable to carry out dry homogenization of the tanning substance and the nitrogenous feed before incorporating the water. In practice the feed, consisting, for instance, of an oil-seed cake, a blood meal, alfa-alfa, etc., is ground to a fine particle size. The tanning substance is then mixed with it until it is evenly colored and then the water is incorporated.

The addition of water to the previously dried homogenized mixture of tanning extract and feed constitutes a method of carrying out the invention which is sometimes preferable to that which consists of preparing a separate tanning substance which is progressively added to the protein.

In this latter case, the formation of lumps is sometimes witnessed, which results in the tannin being spread unevenly through the feed. For instance, by carefully dry homogenizing 100 parts of powdered cake with 15 parts of powdered chestnut tannin an even color is obtained. By progressively incorporating, while stirring, 250 to 300 parts of water, an even colouring of all the particles was then obtained. On the other hand, for 100 parts of feed 10 to 15 parts of powdered chestnut tannin were previously dissolved in 250 to 300 parts of ordinary water. The resulting aqueous solution may include conglomerates of tannin particles, in which case, to obtain an even tanning of the feed, and consequently satisfactory results for the protection of proteins from bacterial degradation, it is first necessary to dissolve these conglomerates before incorporation of the solution with the nitrogenous feed.

After the water has been incorporated into the mixture the mass is stirred for a short time, for from 3 to 5 minutes for instance, until a homogeneous paste with no exudation is obtained. The paste thus obtained is left to stand until analysis shows that there is practically no nitrogenous feed subject to deamination in the upper regions of the alimentary tract (as, for instance, in an artificial rumen) remains in the paste. In some instances, insolubility in water may be an adequate test. A temperature not exceeding 22° C., for 8 to 16 hours is generally used, i.e. the time necessary for the swelling of the proteins and the fixation of the tannin on their molecules. It is preferable not to exceed this period of time in order to avoid the initiation of fermentations which would degrade the proteins and the tannin. Occasional stirring facilities swelling of the proteins and allows any liquid which may have exuded to be reincorporated. Higher temperatures, previously mentioned, can be used where fermentation is not a problem.

In general the higher the dose of tannin the longer the time taken for the liquid to be absorbed.

On the other hand, the feed without tannin, treated with the same amount of water, absorbs it immediately but produces an exudate after two hours. This period of standing is in some cases an essential factor of the paste process of the invention, especially for the treatment of small amounts of crude material. As a general rule when using proteinous feeds, if the moist paste is left to stand for longer than 16 hours, fermentation is seen to start, which degrades the proteins.

Whatever may be the proteinaceous feed and the tannin based substance brought together according to the process of the invention, it is particularly advantageous to control and possibly alter the pH of the reacted mixture in the various stages of the process.

In particular, the aqueous solution of the tanning substance may be alkalinized (up to about pH 8 or 9) to facilitate penetration of the tannin, the mixture of tannin-nitrogenous substance being acidified, for instance, during the period the mixture is left to stand to allow the reaction to take place.

The paste thus prepared is dried until a residual water content of from 8 to 10% is obtained. The drying can be effected in thin layers, either in a circulating air oven or in a standard type atomizer. As far as possible the temperature of the mass during drying should not exceed 80° C. because at higher drying temperatures the protein deteriorates. The temperature should be even lower if longer drying periods are used; for instance, in a dryer it is advisable to operate at between 65° and 80° C. during the first 24 hours and subsequently at about 50° C. for the remaining time. To remove lumps, the dried mass should be finally ground into very fine particles, with a standard grinder for instance, to facilitate its homogeneous incorporation into any feed mixture prepared industrially or on the farm, in the form of meals, pellets or conglomerates for farm animals of all ages (cattles, sheep, goats).

The amount of proteinaceous feeds, tanned according to the process of the invention, to be introduced into the animal food is adjusted so that the concentration of tannin incorporated does not exceed 2.5% in the total dry material daily consumed by the animal, in order to avoid all risk of toxicity.

As animal feeds generally contain sodium chloride it is particularly advantageous to carry out this addition during the operation of mixing the tannin and nitrogenous substance, since sodium chloride promotes the precipitation of proteins.

To illustrate the efficiency, harmlessness and practical usefulness of the process of the invention in farm animal husbandry, the following comparisons were made.

If a peanut cake is introduced into the rumen of a sheep, 48% of its proteins are degraded there into ammonia. The proteins of the same cake, tanned according to the process described above, degraded scarcely 0.5% of this substance. Under identical conditions, an untreated soya looses 25% of its proteins before tanning. It does not produce the slightest trace of ammonia after tanning.

These proteins transformed into complexes by the tannin are liberated by the proteolytic enzymes (pepsin and trypsin) up to a rate practically identical to that which existed before the tanning : 93.5% ± 5.1 against 94.0% ± 3.8 for the peanut cake, 89.4% ± 3.2 against 92.6% ± 2.9 for the soya cake.

The cellulolytic power of the microflora of the rumen is not at all affected by the presence of tanned proteins. Thus, cellulose of an alfalfa hay, introduced alone into the rumen of a sheep, is degraded at a rate of 42.9%. If a non-tanned peanut cake is combined with this hay, this rate rises to 45.6% and, after tanning, 43.6.

For several months, there were distributed to a group of rumen fistulated sheep an identical alimentary mixture presented in agglomerated form and composed of wheat straw, meadow hay, dry pulps of beets, peanut or soya cakes, and mineral salts, so that it constitutes a complete feed covering all nutritive needs of these animals. The cakes furnish 70% of the total proteins of the daily ration and are incorporated therein, whether tanned or not tanned. In the latter case, the complete feed includes 2.5% of tanning substance of chestnut wood produced as cakes treated according to the invention. The examination of the rumen contents taken from these sheep shows that at any hour (up to the sixth) after ingestion of the test meal, its ammonia concentration is about three times lower with the "tanned" cake diets than with the diets of identical cakes not treated with tannin. This strong inhibition of bacterial deamination of the ingested proteins was confirmed by the urea content in the blood which is by 17% lower than with the diet of unprotected cakes.

At no time did the animals show the slightest health trouble or loss of appetite, even after a consumption of several months of feed mixtures containing the proteins protected by the tannin.

These observations of the protein protective properties against bacterial degradation according to the invention, showed the benefit drawn therefrom by the animal, and the safety of the treatment.

The invention is described without in any way being limited by the examples given hereinafter.

A preamble will describe an example of the method of obtaining tanning substances suitable for the requirement of the invention. In this example chestnut wood is treated in a known manner. Similar vegetable matter found in a natural state, such as oak, myrobolan, valonia, quebracho, mimosa, eucalyptus or other plants may be treated in a similar manner.

EXAMPLE 1

Industrial Preparation of Tannic Powder from Chestnut Wood

The wood, without bark, is reduced to chips. The chips are obtained by a machine which tears the wood in a direction perpendicular to the direction of the fibrovascular bundle, this renders the fibre strongly and quickly pervious to water.

The tanning product is then extracted in batteries of double-bottom diffusion tanks, communicating with one another by pipes.

The extraction liquor from the first tank flows into the next one, and so on. Extraction is carried out by water at about 80° C., which flows through the chips in the first tank; the coloured liquor is passed by syphoning onto those in the second tank, and so on; when the liquor drawn from one of the tanks becomes clear, the treated chips are replaced by a new charge of fresh chips and the tank is then placed at the rear end of the battery.

Water-extraction gives a fairly pure tannin containing little sugar, water at a temperature higher than 80° C. may be used, or an autoclave may be used to improve the yield. In this case a dark tannin is usually obtained. The tannin can be bleached with sodium bisulphite, this giving a very soluble tannin. In any case, chestnut tannin is very soluble in cold water. The tannin can also be clarified by treating it with a solution of albumine which fixes, by coagulation, the tannic molecules polymerized during extraction, that is to say, the most coloured ones; the reticular coagulum which forms collects at the bottom of the tank and determines a downward filtration of the tannic liquors.

The tannic liquors are concentrated in vacuum at 60°–65° C. to form a syrup which is dried in atomizer with a circulation of air by 60°–65° C. A very fine powder is thus obtained.

Powder produced from chestnut wood is of a light-brown colour; it is water-soluble; it has an astringent taste and an acid reaction in solution ($-$pH$=$about 3.0) and a molecular weight of about 1550, compared with 1900 of myrobolan tannin, which belongs to the same group. The commercial powder contains 70–75% of pure tanning substance and some "non-tannin" consisting of a major portion of glucide, a very small amount of inorganic material and water (8 to 10%).

EXAMPLE 2

100 parts of pulverized peanut cake, the whole of which passes through sieve ASTM No. 50, and 15 parts of chestnut tannin powder are dry homogenized in a mixing tank provided with blades until an even colour is obtained. 250–300 parts of tap water are added progressively, the mass being stirred until a homogeneous brownish paste is obtained, which has nothing exuding from it, and the stirring is continued for 5 to 10 minutes after all the water has been incorporated. It is left to stand, the mixture is dried and ground.

After 15 hours of incubation in an artificial rumen, out of 100 g of nitrogen contained in untreated cake 48.5 of ammoniacal nitrogen is found, and out of 100 g of nitrogen contained in cake tanned according to the process given hereinabove only 0.4 g of ammonia nitrogen is found.

This example shows that the process of the invention provides a surprising degree of protection for the proteins of the cake. It will be noted that the amount of tannin with respect to the crude nitrogenous feed is 15%.

EXAMPLE 3

100 parts of pulverized soya cake and 15 parts of chestnut tannin powder are dry homogenized until an even colour is obtained. 250–300 parts of tap water are added progressively, the mass being stirred until a homogeneous brownish paste is obtained. The incorporation of water should be watched carefully, as this is not so easily incorporated as in the case of groundnut (example 2), so that there is no supernatant water.

The mass is left to stand, then dried and ground. After 15 hours in an artificial rumen, 100 g of nitrogen contained in the soya cake give 25.3 g of ammonia nitrogen, while 100 g of the same cake tanned according to the invention give rise to no formation of ammonia nitrogen.

This example also shows that the incorporation of 15% of tannin in soya cake, in accordance with the invention, gives effective protection to the proteins of the cake.

EXAMPLE 4

100 parts of powdered cow milk casein or powdered milk, and 15 parts of chestnut tannin powder are dry homogenized until an even colour is obtained. Tap water is added, it is left to stand, dried and ground under the same conditions as in example 2 (groundnut cake at 15%).

After 15 hours in an artificial rumen 100 g of untreated casein nitrogen produce 80.4 g of ammonia nitrogen.

It is known, moreover, that casein proteins are almost totally deaminated in the paunch of ruminants.

This example also shows the effectiveness of the process of the invention in the protection of casein proteins.

EXAMPLE 5

100 parts of blood meal are dry homogenized with 15 parts of chestnut tannin powder until an even colour is obtained. Tap water is added, it is left to stand, dried and ground under the same conditions as in example 2 (peanut cake at 15%). The tanning thus obtained provides an effective protection of food proteins against bacterial degradation.

Similar results are obtained with fish or meat meals, as nitrogenous feeds, or with tannins extracted from oak, myrobolan or quebracho as tanning substances.

EXAMPLE 6

100 parts of fish or meat meal are dry homogenized with 10 parts of chestnut tannin powder until an even colour is obtained. 250–300 parts of tap water are progressively added, stirring the mass until a homogeneous brownish paste is obtained, with no exudate, and stirring is continued for 5 to 10 minutes after all the water has been incorporated. It is put to stand, the mixture is dried and ground. Tanning carried out according to the invention in an amount of 10% by weight of tanning substance with respect to the crude nitrogenous feed ensures effective protection of proteins against bacterial degradation.

Similar results are obtained by tanning soja or linseed cake with amounts of about 10% by weight of tannin.

EXAMPLE 7

This example is given as a comparison to show the influence of the amount of tannin which should be incorporated into the nitrogenous feed. A peanut cake was used into which 6% by weight of chestnut tannin was incorporated.

100 parts of powdered peanut cake and 6 parts of chestnut tannin powder were dry homogenized until an even colour was obtained, water was added, it was left to stand, dried and ground under the same conditions as in example 2 (peanut cake at 15%).

After 15 hours of incubation in an artificial rumen, out of 100 g of nitrogen from untreated cake 48.5 g of ammoniacal nitrogen was found; 100 g of nitrogen from cake tanned at 6% gave 27.2 g of ammoniacal nitrogen.

The protection of proteins against bacterial degradation was therefore insufficient.

EXAMPLE 8

In this example, which is given as a comparison, no tanning was carried out.

100 parts of peanut cake had 250 to 300 parts of ordinary water added to them, but no tannin. Treatment was carried out under the same conditions as in example 2 (peanut cake at 15%), the only difference being that no tannin was added.

After 15 hours of incubation in an artificial rumen, 100 g of nitrogen from cake having undergone the above-mentioned treatment gave 46.8g of ammonia nitrogen against 48.5 g per 100 g of nitrogen of natural peanut cake (raw material).

Untanned proteins are therefore very much degraded.

Examples 9 to 11 which follow are given to show the influence of the amount of water incorporated into the mixture of nitrogenous feed and tannin.

As a preliminary, 100 parts of powdered feed and 10 to 15 parts of chesnut tannin were dry homogenized.

EXAMPLE 9

Amounts of water used were equivalent to 2.5 to 3 times the weight of the feed.

Top water was added to the dry feed-tannin mixture, in a proportion of 250 to 300 parts of water to 100 parts of feed. The mixture was stirred progressively incorporating the water until a thick, homogeneous brownish coloured paste was obtained, with no supernatant liquid. The mass did not give off an exudate after standing for 8 to 16 hours.

EXAMPLE 10

An insufficient amount of water was used, equivalent to 1 to 2 times the weight of feed.

Tap water was added to the dry feed-tannin mixture in the proportions of 100 or 200 parts of water for 100 parts of feed. After stirring the mixture was powdery and the colour was not homogeneous; many of the feed particles retaining their natural colour, while others were coloured brown. Fixation and distribution of tannin were irregular. Tanning was not satisfactory. Protection of protein against bacterial degradation was therefore not effective.

EXAMPLE 11

An excess amount of water was used, equivalent to 4 times the weight of the feed.

Tap water was added to the dry feed-tannin mixture in a proportion of 400 parts of water for 100 parts of feed. After stirring the presence of supernatant water was established. Even after standing for several hours, and repeated stirring, supernatant water always appeared. Tanning is insufficient and unhomogeneous as a certain portion of tannin remains dissolved in the liquid and cannot act on the feed during swelling of the proteins.

Furthermore, there is a loss of soluble proteins in the supernatant.

The following examples show the effect of tanning tretment on the deamination and digestibility of nitrogenous feeds in vivo.

EXAMPLE 12

Another comparative experiment was carried out in vivo using feed containing tanned or untanned soya cake. A group of fistulized sheep consumed the same feed mixture except that the peanut cake of example 2 was replaced by soya cake. The amounts of ammonia nitrogen measured in 100 ml of the rumen fluid were lower by 22% due to action of the tannin.

The total amount of ammonia nitrogen found in the rumen 60 minutes after the meal was 23% lower when the feed contained tannin and the maximum concentration of urea in the jugular blood was lowered by 16%. The total amounts of total volatile fatty acids, acetic and propionic acids found in the rumen after 60 minutes were not significantly different in the presence of protected protein, only butyric acid was lower by 21%.

EXAMPLE 13

In this example, an experiment was carried out on adult sheep to compare the digestibility of tanned and untanned feeds.

A group of fistulized adult sheep consumed the same feed mixture containing groundnut and soya cakes, which were either tanned or untanned. The presence of tanned cake in the mixture did not alter the balance of digestion, that is, the total amount of feed digested in the alimentary tract.

The digestibility coefficients of diets of untanned cake and tanned cake were respectively as follows: 60.3 and 60.2% for dry matter, 62.3 and 62.4% for organic matter, 50.6 and 52.5% for crude fiber or cellulosic materials. It is therefore established that the presence of tannin in no way alters the utilisation of the carbohydrates, and particularly the cellulose of fodders introduced into the ration(63% of the total dry matter) fodders which form the basic feed in feeding ruminants.

EXAMPLE 14

In this example, an experiment was carried out on the enzymatic digestibility in vitro of the proteins of tanned and untanned cake.

The nitrogen of a peanut cake, tanned at 15%, was digested at 93.5% in vitro by the successive action of proteolytic enzymes; pepsin and trypsin. This same cake, treated with water, dried and ground under the same conditions as the tanned cake, was digested at 94%. The nitrogen of a soya cake, tanned at 15%, was digested at 89.4% by proteolytic enzymes, whilst that of the same cake, treated by water, was digested at 92.5%.

EXAMPLE 15

Tanning with formol (30% technical formaldehyde solution). 100 parts of finely pulverized peanut cake are dry homogenized. 300 parts of water containing variable amounts of a 30% technical formaldehyde solution are added progressively, the mass being stirred continuously until a homogeneous, soft paste is obtained. This is left to stand 16 to 20 hours and then examined to see if the liquid phase has been completely absorbed into the mass. It is dried at a temperature not in excess of 80° C. The dried product obtained is ground.

(a) Effect on deamination

A test quantity of the finished product is placed in an "artificial rumen". After 15 hours incubation at 39° C. in a $CO_2$ saturated medium, and in the presence of an inoculum of sheep rument juices, the following levels of deaminated nitrogen from the cake were obtained, as a function of the dose of formaldehyde used: these levels are expressed in relative value (%) with respect to the 0 formaldehyde control taken as base 100.

| ml of 30% technical formaldehyde solution per 100g cake | 0 | 0.6 | 0.8 | 1.0 | 1.2 | 1.4 | 1.5 | 1.6 | 1.7 | 1.8 | 1.9 | 2.0 | 10 | 40 |
|---|---|---|---|---|---|---|---|---|---|---|---|---|---|---|
| cake nitrogen deaminated, in relation to the 0 formaldehyde control | 100 | 89 | 83 | 45 | 31 | 18 | 14 | 11 | 11 | 9 | 7 | 0 | 0 | 0 |

(b) Effect on cellulolysis (cellulose degradation)

The effect of tanned cake with various amounts of formaldehyde on the in vitro digestion of cellulose contained in a conventional wheat straw feed, which is particularly rich in cellulose, after 24 hours incubation in an artificial rumen. The following values of cellulolysis, expressed as a relative value with respect to an 0 formaldehyde control taken as base 100, are obtained as a function of the dose of formaldehyde to tan the cake:

| ml of 30% technical formaldehyde used to tan 100g of cake | 0 | 0.6 | 0.8 | 1.0 | 1.2 | 1.4 | 1.5 | 1.6 | 1.7 | 1.8 | 1.9 | 2.0 | 104 |
|---|---|---|---|---|---|---|---|---|---|---|---|---|---|
| cellulolysis calculated on the basis 100 for the 0 formaldehyde cake | 100 | 105 | 104 | 102 | 97 | 98 | 98 | 97 | 97 | — | — | 83 | 69 | 0 |

(c) The effect on the vitro peptic solubility of the protein.

| Dose of formol used for the tanning in ml % of cake | 0% | 2% | 10% | 40% |
|---|---|---|---|---|
| Percentage of solubilized N | 94.0 | 93.0 | 91.2 | 89.7 |

It is thus seen that the presence of tannin does not affect significantly the digestion by proteolytic enzymes of the proteins of the cake.

The following examples illustrate the use of synthetic tanning agents, such as mono- or dialdehydes on a tanned protein, such as peanut-cake. Other synthetic organic tanning agents and proteins give similar results.

Since a 2% dose of formol completely inhibits the deamination of the peanut cakes, there is hardly any risk of the digestibility of treated peanut proteins being decreased

EXAMPLE 16

Tanning with glyoxal (30% commercial solution)

100 parts of finely pulverized peanut cake are dry homogenized. 300 parts of water containing various amounts of a 30% commercial glyoxal solution are added progressively, with continuous stirring, until a homogeneous, soft paste is obtained. It is left to stand for 16 to 20 hours, and then examined to see if the liquid phase has been completely absorbed into the mass. This is dried at a temperature not in excess of 80° C. The dry product obtained is ground.

The finished product is tested in the manner described in the Example 15.

(a) Effect on deamination

As a function of the dose of glyoxal used, the following relative amounts of nitrogen in the cake are deaminated. Results are expressed in a value relative to the 0 glyoxal control taken as basis 100.

| ml of 30% commercial glyoxal solution per 100g of cake | 0 | 2 | 3 | 4 | 5 | 6 | 10 | 40 |
|---|---|---|---|---|---|---|---|---|
| deaminated cake nitrogen referred to the 0 glyoxal control taken as a basis 100 | 100 | 50 | 24 | 15 | 8 | 4 | 0 | 0 |

(b) Effect on cellulolysis

As a function of the dose of glyoxal used, the following values of cellulolysis are observed, expressed in a relative value with respect to the 0 glyoxal control taken as basis 100:

| ml of 30% commercial glyoxal per 100 g of cake | 0 | 2 | 3 | 4 | 5 | 6 | 10 | 40 |
|---|---|---|---|---|---|---|---|---|
| cellulolysis calculated on the basis 100 for the 0 glyoxal cake | 100 | 101 | 100 | 95 | 92 | 87 | 61 | 0 |

(c) Effect on the in vitro peptic solubility of the protein

| Dose of glyoxal used for the tanning in ml % of cake | 0% | 2% | 10% | 40% |
|---|---|---|---|---|
| Percentage of solubilized N | 94.3 | 93.0 | 92.6 | 91.6 |

EXAMPLE 17

Tanning with glutaraldehyde (25% commercial solution)

100 parts of finely pulverized peanut cake are dry homogenized. 350 parts of water containing variable amounts of a 25% commercial solution of glutaraldehyde are added progressively, with continuous stirring until a homogeneous, soft paste is obtained. With 300 parts of water the paste is insufficiently soft. It is therefore necessary to increase the amount of water to 350 parts in order to obtain a good reaction formulation.

The finished product is tested in the manner described in example 15.

(a) Effect on Deamination

As a function of the dose of glutaraldehyde used, the following levels of deaminated nitrogen in cake are obtained; these are expressed in relative value to the 0 glutaraldehyde taken as base 100.

| ml of 25% commercial glutaraldehyde solution per 100 g of cake | 0 | 2 | 3 | 4 | 5 | 6 | 10 | 40 |
|---|---|---|---|---|---|---|---|---|
| nitrogen in deaminated cake based on glutaraldehyde control 0 | 100 | 66 | 44 | 28 | 13 | 2 | 0 | 0 |

(b) Effect on cellulolysis

As a function of the dose of glutaraldehyde used, the following levels of cellulolysis are observed expressed in relative value with respect to the glutaraldehyde control 0 taken as basis:

| ml of 25% commercial glutaraldehyde solution per 100g of cake | 0 | 2 | 3 | 4 | 5 | 6 | 10 | 40 |
|---|---|---|---|---|---|---|---|---|
| cellulolysis calculated on the basis 100 for 0 glutaraldehyde cake | 100 | 102 | 97 | 98 | 97 | 91 | 80 | 0 |

(c) Effect on the peptic solubility in vitro of the protein

| Dose of glutaraldehyde used for the tanning in ml % of cake | 0% | 2% | 10% | 40% |
|---|---|---|---|---|
| Percentage of solubilized N | 94.0 | 92.5 | 88.9 | 87.2 |

The minimum dose of glutaraldehyde which completely inhibits deamination is less than 10%. Within this tanning limit the digestibility of treated peanut proteins is not decreased to any appreciable extent.

Examples of tanning synthetic amino acids:

EXAMPLE 18

Amino acid treated: L-lysine-mono hydrochloride

25–30% of the nitrogen contained in L-lysine-HCl is deaminated in an artificial rumen. It is impractical to tan lysine in its natural state because due to its high solubility this would require very high levels of the tanning substance. Even a dose of 75% of chestnut tannin powder does not completely stop deamination of lysine which, in an artificial rumen, reaches a value of about 8–10%. In theory, therefore, equal amounts of tannin and lysine should be used, but such a high ratio may have serious physiological effects on the animal But it has been discovered that a preliminary adsorption of lysine on a suitable protein support only requires a small dose of chestnut tannin powder, as can be seen from the following examples and similar improved results would be obtained in requiring less tanning agent for protecting compounds such as urea, glycine, and other very soluble N containing animal feeds.

EXAMPLE 19

An amount of L-lysine monohydrochloride, corresponding to 25% of the final product, in solution in 250 parts of water, is incorporated into 100 parts of wheat bran which is a support for the lysine compound. The mass is homogenized and allowed to stand for 1 hour. The desired doses of chestnut tannin solubilized in 250 parts of water are then added. Maximum homogenization is then carried out. The mass is allowed to stand for 16 hours. The paste is dried at a temperature not exceeding 80° C. until a residual moisture content in the range of 5 to 7% is obtained. The final product is finely powdered by conventional grinding. The parts of each of the ingredients varied with the dose of tannin used as shown in the following table:

| % Tanning | 0 | 2.9 | 2.9 | 5.9 | 9.2 |
|---|---|---|---|---|---|
| Bran | 100 | 100 | 100 | 100 | 100 |
| L-Lysine | 33 | 0 | 35 | 36 | 38 |
| Tannin | 0 | 3 | 4 | 8.5 | 14 |
| Water | 500 | 500 | 500 | 500 | 500 |

A suitable test amount of the final product is tested in an artificial rumen. After 15 hours of incubation, the following percentage of nitrogen degraded into N-NH$_3$ are observed:

| Dose of tannin used in % of support enriched with L-Lysine HCl | 0 | 0 | 2.9 | 2.9 | 5.9 | 9.2 |
|---|---|---|---|---|---|---|
| Value of L-lysine adsorbed on the support | 0 | 25 | 0 | 25 | 25 | 25 |
| Deaminated N % total N in the substrate | 9.7 | 18 | 0.1 | 6.5 | 1.0 | 0 |

It is thus seen that deamination of the proteins of the support alone reaches about 10% and that it only requires about 3% tannin to block it; the substrate comprising 25% of untanned L-lysine HCl is deaminated to 18%. This same product is not deaminated further after tanning at a dosage of 9.2% of chestnut tannin powder and the lysine is thus completely protected.

EXAMPLE 20

An amount of L-lysine monohydrochloride, corresponding to 25% of the final product, in solution in 250 parts of water, is incorporated into 100 parts of linseed cake. The mass is homogenized and allowed to stand for 1 hour. The desired doses of chestnut tannin solubilized in 250 parts of water are then added. Maximum homogenization is then carried out. The mass is allowed to stand for 16 hours. The paste is dried at a temperature not exceeding 80° C. until a residual moisture content in the range of 5 to 7% is obtained. The final product is converted to a fine powder by conventional grinding. The proportions of each of the ingredients varied with the dose of tannin used, as shown in the following table:

| % Tannin | 0 | 5.5 | 6.8 | 9.8 | 12.0 | 15.0 |
|---|---|---|---|---|---|---|
| Linseed cake | 100 | 100 | 100 | 100 | 100 | 100 |
| L-lysine HCl | 33 | 0 | 37 | 38 | 40 | 42 |
| Tannin (amount) | 0 | 5.8 | 10 | 15 | 19 | 25 |

A suitable test amount of the final product is tested in an artificial rumen. After 15 hours of incubation, the following percentages of nitrogen degraded into N-NH$_3$ are observed:

| Dose of tannin used in % of support enriched with L-lysine HCl | 0 | 0 | 5.5 | 6.8 | 9.8 | 12 | 15 |
|---|---|---|---|---|---|---|---|
| Value of L-lysine adsorbed on the support | 0 | 25 | 0 | 25 | 25 | 25 | 25 |
| Deaminated N % total N in the substrate | 38.8 | 27.7 | 0 | 0.7 | 0 | 0 | 0 |

Deamination of untreated linseed cake proteins is very high: 38.8%. The N level of L-lysine degraded into N-NH$_3$ is lower than about 25% which explains why linseed cake with 25% of this amino acid adsorbed only deaminated 27.7%. 5.5% of chestnut tannin is sufficient to eliminate degradation of the protein of the support alone, whereas 7–8% was sufficient to eliminate degradation after adsorption of 25% of L-lysine HCl.

The preceeding examples prove the effectiveness of the tanning process of the invention for the protection of consumable foodstuffs against bacterial degradation in the alimentary tract of animals.

It will be understood that the term "feed" is being used throughout this disclosure in its broad sense to include at least some nutritive material i.e. material that can be absorbed or taken into the body of an animal and thereby serves for purposes of growth and maintenance of the vital processes.

While the two immediately preceding examples have related to L-lysine monohydrochloride, the disclosed techniques of protecting very water soluble nitrogenous feeds on a support can be applied to other amino acids and products containing them and, as well, to their salts and esters such as basic L-lysine, sulfated amino acids such as cystine DL-methionine etc., and their counter parts such as the hydroxymethyl analogue of methionine; further L-threonine L-tryptophane, L-leucine and L-isoleucine and the hydrochlorides and esters thereof.

Likewise many standard experiments have been carried out with the nitrogenous feed-tannin complexes hereof in addition to those set out hereinbefore. For example, in tests using artificial rumen tests have been carried out analogous to those of the Examples not only with the complexes formed with soya bean or peanut cake but also with complexes formed wth casein, skim milk, sunflower seed cake, rapeseed cake, linseed cake and alfalfa. Wholly analogous results were obtained, the protection of the nitrogenous content of casein being especially notable. Tests were carried out, also, by standard procedures with sheep using a condensed agglomerated feed of which 70% was obtained from tanned and untanned soya bean and peanut cake. The results were equally as favorable as those reported previously herein. Standard tests were carried out with sheep using an experimental and an equal number of control animals using a combination of nutrients including hay and various percentages of an agglomerated feed containing 10.65% of total nitrogen, 52% of which was provided by tanned and untanned skim milk. It was found the total percentage of apparently digestible nitrogen retained by the tanned skim milk was increased 47.5% while the increase in the nitrogen absorbed based on the totality of nitrogen, was 39.0%. Yet the presence of the tannin hardly affected the digestive utilization coefficient of the organic material even though the total amount of nitrogenous material extracted from the feed was very slightly lowered. Further experiments were carried out on alpine kids weaned early, i.e. 4 to 6 weeks. The tests were carried out on four groups of animals containing four animals in each group. The animals were placed in individual pens and given diets containing tanned and untanned skim milk. In order to make the effects of complexing the milk with tannin as clear as possible a morning feeding using a high level nitrogenous diet was evaluated and, as well, two diets of low level nitrogen content. Concentrated proteinous feeds containing tanned and untanned powdered milk, which provided 50% of the protein of the diet, were used in the test. The evening meal consisted of energy giving feed consisting of cereals and hay so as to provide a balanced diet. Tests were conducted on the effects of the morning meal during the 6–22 week age period and were evaluated at the end of the 14 week age period and at the end of the 22 week age period. During the testing period the four groups, respectively, designated for convenience as I, II, III and IV, were fed 140, 110, 110 and 90 Scandinavian feed units. Groups I and II (control groups) were fed an untanned and groups III and IV were fed a tanned diet. The diet of group IV appeared in adequate but still compared favorably with some of the higher control diets. The test results most favorable to the formation of a tanning complex were obtained by comparing control groups I and II with groups III during the first 8 week period. For instance, during the first 8 weeks the comparison between group I and group III for weight gain was +39.5% and +52% for nitrogen efficiency. At the end of the 22 week period the comparison was somewhat less favorable but still was +32% and +40% respectively.

the foregoing illustrations of the formation of complexes between nitrogen feeds and organic tanning substances and the evaluatio of these complexes when used in animal feeds is considered sufficient to illustrate applicants' discoveries, but are not intended to be exhaustive for these embodiments are only illustrative of the totality of the experimental data and the discoveries made in this invention.

A theory as to the nature of the complexes formed in this invention is not necessary to an understanding of the invention. Yet the nature of the complexes of the invention has been discussed earlier herein but, as is often the case, the exact nature of the complexes is not always known. The functional groups in nitrogenous feeds such as proteins, amino acids, and the like are known; and, as well, the functional groups in natural and synthetic organic tanning agents are known. On the basis of this knowledge and extensive research, reported and unreported, it can be assumed that depending on the nature of the nitrogenous feeds and the organic tanning agents the bonds customarily are hydrogen bonds, ionic bonds, and covalent bonds formed between such functional groups such as —NH$_2$, —CO—, OH, —CHO and the like such as appear in proteins, amino acids, $\alpha$-peptide groups and natural and synthetic tannins. Extensive evaluations of the nature of the bonds formed between proteins of hides (collagens) and tanning agents have been made, and are consistent with the foregoing conclusions.

EXAMPLE 21

Protective treatment of the feed may be effected with plant tannin in a very moist medium.

The technique of treatment is carried out as follows: a solution containing variable amounts of tanning substances is added progressively, according to its nature, to the ground homogenized feed at rates of 2 to 5 times the weight of said feed, the mass being stirred continuously until a homogenous, soft paste is obtained. This is left to stand for 16-20 hours at room temperature in order to encourage maximum adherence of the tanning substance to the protein and maximum swelling of the latter. The liquid phase should be completely absorbed by the mass. The paste is then dried at a temperature no higher than 80° C. We compared:

(a) with groundnut cake, the effect of the nature of the tannin(chestnut tannin and quebracho tannin) on the effectiveness of the protection obtained;

(b) with chestnut tannin, the behaviour of various proteins of plant origin (soya, rapeseed, viz. colza, linseed, groundnut and sunflower seed cake) and animal origin (casein, powdered milk).

The results of the deamination of the various preparations are given in FIG. 1. It shows that quebracho tannin appears to be slightly less effective than chestnut tannin and that the behaviour of proteins varies according to their nature.

Untreated groundnut or sunflower seed proteins are deaminated to about 60%. A minimum dose of 14-15% tanning extract is necessary to give them complete protection, rapeseed proteins require a maximum of 10%.

As the nitrogenous fraction subjected to degradation is substantially smaller for soya and linseed cakes, insolubilization and complete blocking of its deamination can be obtained with a maximum rate of 6% tanning extract.

The effective protection of dry skim milk proteins requires a high percentage of tanning powder (16%). Substantial deamination of very highly soluble casein is difficult to avoid, even after tanning at 30 and even 50%. The latter dose, which is very high, still leaves about half the nitrogen in the casein exposed to deamination. FIG. 1, A through H, shows the effect of treatment on microbial degradation of protein in the rumen. In these graphs, (ches) means tanning with a tanning extract of chestnut and (que) means tanning with a tanning extract of quebracho.

EXAMPLE 22

Treatment of groundnut cake in a low moisture medium not requiring subsequent drying (with chestnut tanning powder).

Technique: The groundnut cake and chestnut tanning powder (4 to 8%) are mixed dry, or with 4 or 8% water alone, or with sugar beet molasse, in a high speed mixer. The mixer is left to stand. The results are given in the table below:

| Dose of Tannin p.100 cake | Dose of water p.100 cake | Solubility in Saliva Base 100 untreated Product | Deamination base 100 untreated cake in rumen in Vitro |
|---|---|---|---|
| 4% | 4% | 82.7 | 79 |
| 4% | 8% | 80.5 | 73.4 |
| 8% | 4% in 12% molasse | 37.4 | 39.1 |

A parallelism is observed between the reduction of solubility and the reduction of deamination.

This technique permits deamination of the cake to be reduced.

EXAMPLE 23

Treatment of groundnut cake in a low moisture medium not necessitating subsequent drying (with spraying with a 50% chestnut tannin solution).

The groundnut cake is granulated in the form of crumbs (without oil or with 2% oil) obtained by passing it through a very short 2.5 mm pelleting die.

Technique: The concentrated tannin solution is sprayed on the cake stirred in a horizontal ribbon mixer.

The results are given in the following table:

|  | Dose tannin p.100 Substrate | Water added p.100 Substrate | Solubility Saliva base 100 untreated cake | Deamination in Vitro Rumen Base 100 Untreated Cake |
|---|---|---|---|---|
| Crumbs | 4 | 4 | 68 | 74 |
| Crumbs + 2% Oil | 8 | 8 | 39 | 44 |

EXAMPLE 24

Protective treatment can be effected with aldehydes in a high moisture medium.

The protective technique adopted is identical to that of Example 21. We compared: (a) with groundnut cake, the effect of the nature of the aldehyde (formaldehyde, glyoxal and glutaraldehyde): (b) with formaldehyde, the behaviour of various protein of plant origin (groundnut, soya, soya protein cake) or animal origin (powdered skimmed milk, caseins).

The results concerning the deamination of the various preparations are summarized in FIG. 2, A through D, which shows the effect of the dose of an aldehyde on the deamination of protein in "in vitro" rumen medium. Total inhibition of deamination of groundnut proteins is obtained with a dose of 2% commercial formol or 6% glyoxal or glutaraldehyde. Soya been meal and dry skim milk are markedly less vulnerable to bacterial deaminases and required half as much formol (1%), whereas casein, whatever the technique used for preparation, required a dose double (4%) that for groundnut and four times that for dry milk, although it only contains 2.5 times more nitrogen than the latter.

EXAMPLE 25

Protective treatment with formol in a low moisture medium requiring little or no subsequent drying.

Technique: A commercial or diluted formol solution is added to the product to be protected which is stirred in a high speed mixer. Results: The following table gives the nature of the protein treated, the dose of formol added, the total moisture content of the product after incorporation of formol and deamination in vitro in a rumen, base 100, obtained after the tanning agent and the protein have been left in contact, at rest, for a sufficiently long period of time to obtain maximum protection.

This technique enables proteins to be effectively protected from degradation in a rumen medium without having to effect substantial drying of the product after treatment.

|  | Formol added p.100 substrate | Dose of dilute formol added p.100 substrate | Total moisture content after formol incorporation | Deamination base 100 untreated cake |
|---|---|---|---|---|
| Groundnut cake | 1.4 | 1.4 | 10 | 20 |
| " | 1.4 | 10 | 18.5 | 1 |
| " | 1.2 | 5 | 13.5 | 7 |
| " | 1.2 | 10 | 18.5 | 7 |
| " | 1.2 | 15 | 23.5 | 3 |
| " | 1.0 | 10 | 18.5 | 20 |
| Soya protein | 1 | 2.5 | 8.5 | 63 |
| " | 3 | 7.5 | 13.5 | 5 |
| " | 4 | 10 | 16 | 2 |
| Soya cake | 0.33 | 3 | 14 | 37.5 |
| " | 0.67 | 6 | 17 | 21 |
| " | 1.0 | 9 | 20 | 10 |
| " | 0.33 | 7 | 15 | 38 |
| " | 0.5 | 7 | 15 | 19 |
| " | 0.33 | 2.5 | 5 | 83 |
| " | 0.67 | 5.0 | 8 | 52 |
| " | 1.0 | 7.5 | 10 | 24 |
| Colza cake | 0.33 | 3 | 14 | 80 |
| " | 0.67 | 7 | 18 | 44 |
| " | 1.0 | 10 | 21 | 30 |
| " | 1.33 | 13 | 24 | 11 |

EXAMPLE 26

Protective treatment of ground dry cake with gaseous formaldehyde.

Technique: The crude soya cake is stirred in a vertical mixer provided with a suitable device for introducing a gas at the lower level. Gaseous formaldehyde, obtained by the vaporization of a formol solution introduced drop by drop into a heated tube is introduced through said device. Samples are taken at regular time intervals from the mixer.

Results: Deamination of said samples is studied in rumen in vitro. The results are summarized in the following table.

| Dose of formol (ml) p.100 g Cake | Deamination Base 100 |
|---|---|
| 0 | 100 |

| Dose of formol (ml) p.100 g Cake | Deamination Base 100 |
|---|---|
| 0.33 | 73 |
| 0.67 | 42 |
| 1.0 | 28 |
| 1.33 | 16 |
| 1.67 | 8 |
| 2.00 | 6 |
| 2.33 | 1 |
| 2.67 | 0 |

Conclusion: Protection of crude soya cake can be obtained by treating the cake with gaseous formaldehyde in a suitable mixer under controlled reaction conditions.

EXAMPLE 27

Treating ground raw soya cake with a formol solution placed in an organic solvent, followed by removal of the solvent by filtration and heat drying. p Technique: one part of the cake is placed in a reactor and stirred with solvent in the ratio 1:4 (w/v). Then, 0.5 or 1% of a formol solution is added to the cake and stirring is continued for one hour. The mass is left to stand for 2 hours and filtered through textile and washed with the solvent (2 volumes per weight of cake). After filtration under vacuum, the residue is dried by infra red to a constant weight.

Results: The table below gives the deamination rate of the soya cake (calculated on base 100 for the initial control cake), treated in various organic media with 0.5 and 1% formol solution and compared with the technique used in Example 21.

| Solvent medium | 0.5% formol cake | 1.0% formol cake |
|---|---|---|
| Ethanol | 88 | 74 |
| Acetone | 70 | 47.5 |
| Ethyl ether | 51.5 | 27 |
| B petroleum | 39 | 18 |
| Hexane | 36 | 18 |
| Water (technique of example 21) | 45 | 19.5 |

Conclusions: The influence of water solubility in the various solvents appears to be the main factor of protective efficiency. When the solvent dissolves the water (and the formol) treatment under the conditions used is too slow, the uncombined formol being removed in the filtrate; treatment is then insufficient and it would be necessary either to increase the amount of formol, or to increase the reaction rate of treatment (by heating for example). When the formol (or the water) is insoluble in the solvent (petroleum B, hexane) similar protection is obtained to that obtained in Examples 24 and 27.

EXAMPLE 28

A crude ground soya cake, placed in an organic solution is stirred with solvent (ratio 1:25 in w/v) then, 0.5 or 1% of a formol solution is added. Stirring is continued for one hour and the mixture is left to stand for a minimum of 3 hours. The reactor is then heated to remove the used solvent removal is finished in vacuum.

Results: The table below shows deamination of soya cake (calculated on Base 100 for the initial control cake treated in various organic media with 0.5 or 1% formol solution and compared with the technique used in Example 21.

| Solvent medium | 0.5 formol cake | 1.0% formol cake |
|---|---|---|
| Ethanol | 42.5 | x |
| Acetone | 29 | 16 |
| Ethyl Ether | 35 | 19 |
| Petroleum B | 50 | 17 |
| Water (according to the technique used in example 21) | 45 | 19.5 |

Conclusions: Treatment can be effected by incorporating formol in an organic medium. If the solvent is removed by distillation, the nature of the solvent appears to have little influence.

EXAMPLE 29

The effect of the absence of water on the efficiency of treatment with formaldehyde in an organic medium.

It was shown in example 28 that efficient tanning can be effected by incorporating formol in an organic medium with a soya cake. In this case, the efficiency of the treatment was similar to that observed in example 24 (treatment in a high moisture medium), although only a small amount of water was present during the reaction (about the 10% of the initial moisture of the cake). The following example is intended to show whether, with a very small amount of water, it is possible to protect proteins by treatment with formaldehyde. In this example we used:

(1) a casein prepared by the Hammarstein method as control protein. The water contained in the casein (about 5%) is first removed as thoroughly as possible by azeotropic distillation with hexane. (2) a formaldehyde in methanol solution having the following composition: formaldehyde 46.5%, methanol 44.5%, water 9%. (3) an anhydrous solvent intended to permit intimate contact between the formaldehyde and the protein. Said solvent is either hexane or anhydrous ethanol. Said solvent is removed by distillation as in example 28. The following procedure is used: 50 g casein and 250 ml hexane are placed in a reactor provided with stirring and heating devices; distillation is conducted to remove water until the end of the azeotrope (5.4% water) is about 40 cc of the distillate.

In the case of tanning in a hexane medium, 1 ml of the formaldehyde in methanol solution is added drop by drop to said casein in an anhydrous medium. The mixture is reacted for one day, stirring the medium, the hexane then being removed by dry distillation. The casein thus treated is then dried at low temperature in an oven, 50° to 60° C.

In the case of tanning in an anhydrous ethanol medium, when the hexane is practically removed by distillation, 200 cc anhydrous ethanol is added and the ethanol-hexane azootrope is distilled (about 40 cc of distillate). The equivalent of 1 cc of commercial formaldehyde in methanol solution, previously diluted in 50 cc absolute ethanol, is then added. The medium is left to stand for about one day with stirring, followed by distillation to remove the maximum amount of solvent. The casein so treated is then dried in an oven at low temperature.

In both cases a control is made, following the same procedure, but without adding formaldehyde, in order to study the possible modifications which the physical treatments may make in the degradability of casein in a rumen medium. The behaviour of the various preparations (control and formaldehyde-treated) is studied in vitro in a rumen and compared with a casein prepared as in example 24 in a very high moisture medium (4 volumes of water) with the same rate of the commercial formaldehyde in methanol solution (1 cc for 50 g of casein).

The results, which are summarized in the following table, show that formaldehyde tanning treatment can be as effective in a practically anhydrous medium as in a highly hydrated medium.

| | Deamination Base 100 in a Rumen Medium | | |
|---|---|---|---|
| | Treatment in Hexane Medium | Treatment in Anhydrous Ethanol medium | Treatment in a High Moisture Medium |
| Control without formaldehyde | 98 | 100 | x |
| + formaldehyde | 52 | 36 | 34 |

The slightly higher efficiency of treatments in a ethanol medium may be due to: the polarity of said media (or the presence of an OH group) which encouurages the chemical reaction and/or a more homogenous reaction owing to the larger solubility of formaldehyde in said media.

EXAMPLE 30

Tanning substances of different chemical character can be associated and the combination effectively protects proteinaceous feeds.

The same processing technique is used as in example 21. The tanning substances used are, either chestnut plant tannin, or formol or an association of both these substances. The amounts of tanning substance used to treat a same groundnut cake and the deamination of the cake observed in an artificial rumen (base 100 untreated cake) are summarized in the following table.

| Nature of the Tanning Substance and Dose p.100 Cake | | |
|---|---|---|
| Chestnut Plant Tannin | Formol | Deamination Base 100 Untreated Cake |
| 0 | 0 | 100 |
| 5 | 0 | 40 |
| 7.5 | 0 | 17 |
| 15 | 0 | 0 |
| 0 | 0.67 | 84 |
| 0 | 1.0 | 60 |
| | 2.0 | 0 |
| 5 | 0.67 | 8 |
| 7.5 | 1.0 | 0 |

The results show that under these conditions the association of different tanning substances can provide said protection and that, in fact, more than an additive effect exists with respect to the protective power of said tanning substances. Thus, whereas 5% chestnut tanning provides 60% protection and 0.67% formol provides less protection (16%) the association of 5% plant tannin and 0.67% formol provides 92% protection. Complete protection is obtained if 7.5% chestnut tannin is associated with 1% formol, rates corresponding to half the doses of said tanning substances necessary to ensure the same protection when used alone.

EXAMPLE 31

Evolution of the degradation of an intimate mixture of cake+diluted formol as a function of time.

A dilute formol solution was incorporated with groundnut cake using the technique described in example 25. In this experiment, the cake was mixed with 10% its weight of dilute formol (dose equal to 1.2% formol).

The evolution of the deamination of the cake was studied in an artificial rumen. Taking as a reference the value 100 for deamination of untreated cake, we found that deamination of the cake amounted to 72% after contact for 6 hours, 20% after 2 days, 8% at the end of a week and 5% after two weeks.

We therefore confirm that, under these conditions, optimum protection is only obtained after a sufficiently long time of contact.

EXAMPLE 32

The relation between solubility and deamination.

Figure 3:
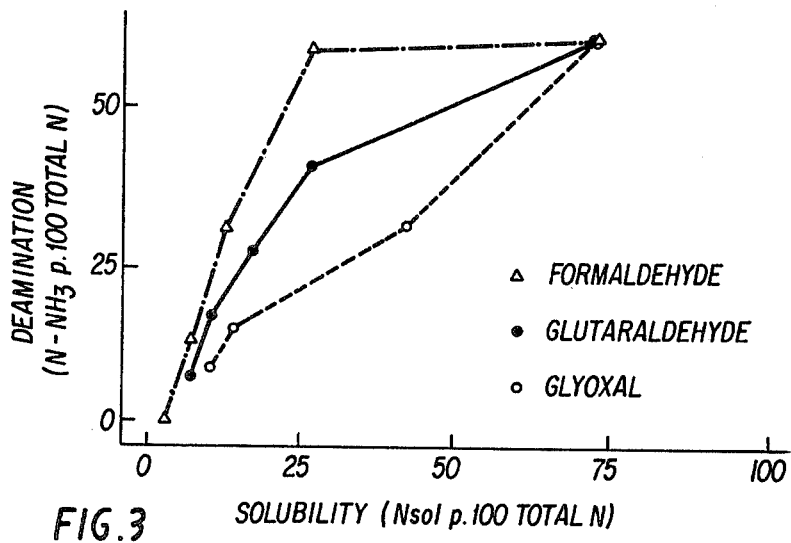
FIG. 3 illustrates the relation between deamination and solubility of groundnut cake treated with variable rates of different aldehydes.

Groundnut cake was treated, using the technique described in example 21 with variable rates of various aldehydes. When tanning was finished, the various preparations were studied to determine their deamination in a rumen medium and their solubility in saliva. The results can be summarized in FIG. 3 which shows the relation between deamination and solubility of groundnut cake treated with variable rates of different aldehydes. It is seen that reduced deamination of the cake is always accompanied by reduced solubility of said same cake. However, the two phenomena can vary in a non-linear manner. Thus, with formol for example, a decrease of almost 50% in the solubility of cake treated with small doses of formol is accompanied by a decrease of only 3% in its degradation in a rumen medium. The physical criteria of solubility cannot therefore be retained to assess the quality of a protective treatment.

EXAMPLE 33

Treatment with glyoxal in a low moisture medium requiring little or no subsequent drying.

Technique: A 15% glyoxal solution is added to low moisture (dry matter+92.2%) toasted colza cake, which is stirred in a mixer with a high speed rotating blade. Samples are taken after the addition of, successively, 0.5-0.72 and 1 g pure glyoxal per 100 g cake.

After a sufficient contact time, the deamination, in an in vitro rumen, of the various products obtained, and their solubility in artificial saliva, are determined and compared with the same untreated control cake.

| Dose of pure glyoxal p.100 cake | Solubility in saliva base 100 untreated product | Deamination base 100 untreated cake in rumen in vitro |
|---|---|---|
| .50 | 80 | 75 |
| .75 | 45 | 65 |
| 1.00 | 29 | 60 |

EXAMPLE 34

The effect of the amount of aldehyde on the deamination of protein and the cellulolytic activity (cellulose degradation) of rumen inoculum.

Figure 4A:
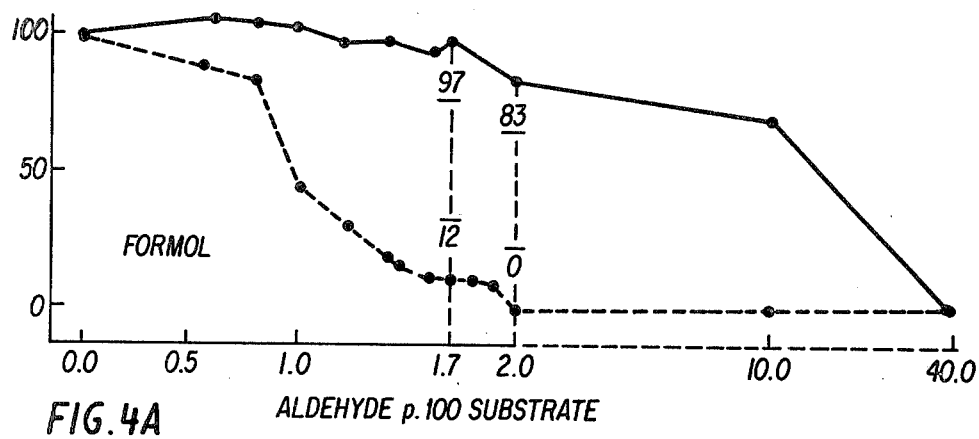
FIG. 4, A through C, illustrates the effect of the tanning treatment of peanut meal by various aldehydes on the deamination and cellulose degradation "in vitro".
Figure 4B:
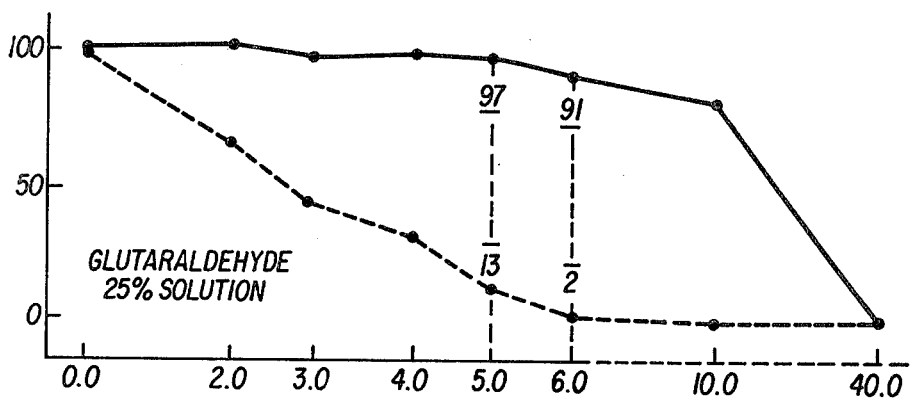
Figure 4C:
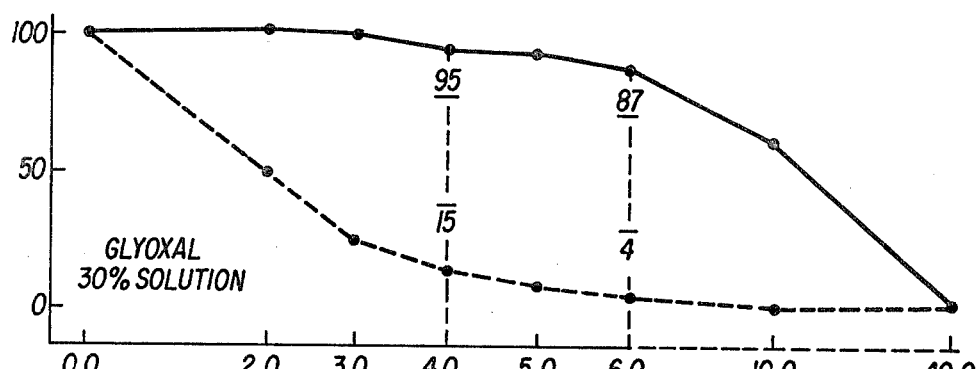

FIG. 4 shows that tanning peanut with formol, glyoxal or glutaraldehyde, which completely block its microbial deamination in vitro, substantially lowers the celluolysis of straw. This lowering effect, which is accentuated by the increase of aldehyde concentration is, on the other hand, negligible for doses slightly below those giving the 0 deamination threshold. In this case, instead of protein protection being complete, only about 85–90% protection is obtained, which is very satisfactory. FIG. 4 shows the effect of the tanning treatment of peanut meal by various aldehydes on the deamination and cellulose degradation "in vitro".

EXAMPLE 35

In vitro

Availability of Tanned Proteins

Proteins are only available to the animal after hydrolysis into amino acids by the proteolytic enzymes of the alimentary tract.

The effect of the dose of tannin product on the peptic solubility of the protein of peanut meal in vitro is given in the following table.

| Tanning substance | Dose | | | | | |
|---|---|---|---|---|---|---|
| | 0 | 2 | 10 | 15 | 30 | 40 |
| Chesnut extract | 94.0 | — | — | 89.2 | 86.3 | |
| Formol | 94.0 | 93.0 | 91.2 | — | — | 89.7 |
| Glyoxal | 94.0 | 93.0 | 92.6 | — | — | 91.6 |
| Glutaraldehyde | 94.0 | 92.5 | 88.9 | — | — | 87.2 |

The treated proteins remain available to the animal. A marked difference between formol and glyoxal on the one hand and glutaraldehyde and powdered chestnut tannin on the other, should be noted.

The first two products do not have a negative action on the peptic digestion of the complex when tanning is effected at the minimum deamination effective dose: the original values are lowered, by about 1%, whereas the dose of glutaraldehyde or chestnut tannin corresponding to the 0 deamination threshold, lowers the peptic digestibility more distinctly (about —5%).

EXAMPLE 36

Checking, in an "in vivo" rumen, the effectiveness of the protection of proteins protected by the process described in example 21.

Groundnut and soya cakes are treated with, respectively, 15% and 6% plant tannin (with the formation of a homogenous paste followed by drying). Said tanned, or untreated control cakes, are used in the composition of a feed compound containing 16% crude protein 70% of which is provided by the cakes. 500 g of said feed is given twice a day to 6 fistulated sheep. After a sufficiently long period of adaptation of the diet, representative samples of rumen fluid were taken before the morning meal, and at given intervals during the 450 minutes following the meal. The N-NH$_3$ and volatile fatty acid content were determined and the results obtained from two measurements per sheep and per diet show that:

1. the production of ammonia is significantly reduced by the treatment. Peaks observed in both cases between the 60th and 90th minute were reduced in the presence of the treated proteins by 45.5% for groundnut and 24.6% for soya, compared with the same unprotecgted proteins.

2. the total volatile fatty acid, acetic acid and propionic acid composition is essentially the same for a same cake, whether protected or not. On the other hand, significant decrease in the production of butyric acid is observed in the case of the treated diets. Said decrease is probably due to the decrease in the deamination of proteins from which said fatty acid is partly derived.

EXAMPLE 37

The effect of tanning treatment with chestnut plant tannin on the digestibility and retention of the treated proteins.

The digestibility of organic substances and nitrogen and nitrogen retention were determined on 6 adult sheep. The diet consisted of 175 g of low qualtiy grass hay and 750 g of a concentrate containing about 12% crude protein, of which tanned powdered milk (or control) provided 40% of the nitrogen. This material, unusual in ruminant feeding, was chosen owing to its high solubility in the rumen and the excellent balance of its amino acids from a nutritional standpoint. The treatment used was similar to that described in example 21. A 15% dose of chestnut plant tannin was used.

The results obtained summarized in the following table, show that as a result of the treatment, nitrogen digestibility was substantially reduced. This observation is met with in many other experiments: its extent depends on various factors, among which the physiological state of the animal and conditions of technological treatment (nature and dose of the tanning substance, drying conditions . . .) play an essential part.

| The effect of tanning treatment on the nitrogen balance of sheep | | |
|---|---|---|
| | Untanned skimmed milk | Tanned skimmed milk |
| g. N ingested/day | 17.9 | 17.2 |
| OM* digested % OM ingested | 74.3 | 72.1 |
| N digested % N ingested | 72.0 | 68.2 |
| N retained % N digested | 16.1 | 23.6 |
| N retained % N ingested | 11.6 | 16.1 |

*OM = organic matter.

Nitrogen retention in the experimental groups was always higher than twith the control whatever method was used for expressing said retention rate: the improvement was very significant whether the nigtrogen retained was compared with the nitrogen digested or ingested. It overcomes the previously mentioned drawback of the product being less digestible owing to the technical treatment with the tanning agent.

Results confirming the advantages of tanning were obtained on dry cows. The basal diet included corn silage and urea. Each cow further received additional feed in the form of soya or colza cake, either protected by tanning with formol or an untanned control. The treatment was applied according to the technique described in example 25, incorporating formol diluted to 15% in a high speed rotating paddle mixer. The doses added, equal to formol, were respectively 1% and 1.3% for soy and colza cake. The results obtained, which are summarized in the following table, demonstrate that digestibility of organic and nitrogenous matter is unaffected by the tanning treatment, and that nitrogen retention is very much improved by the treatment.

| The Effect of Tanning with Formol on the Nitrogen Balance of the cow | | | | |
| --- | --- | --- | --- | --- |
| | Soya cake | | Colza cake | |
| | un-protected | protected | un-protected | protected |
| G.N.ingested/day | 1,436.0 | 1,421.0 | 1,436.0 | 1,422.0 |
| CUD* organic matter | 78.4 | 78.8 | 76.4 | 76.5 |
| CUD* crude proteine | 80.7 | 80.8 | 78.7 | 77.9 |
| N retained % N digested | +5.7 | +19.0 | +7.4 | +14.9 |
| N retained % N ingested | +4.5 | +15.5 | +5.9 | +11.5 |

*CUD : digestibility percent.

EXAMPLE 38

The effect of chesnut tanning of skim milk powder on the growth of ruminants.

Using early weaned kis, a growth experiment was carried out over a 16 week period, with 2 groups of 4 animals weaned at 6 weeks, to test the treatment, the effects of which had already been studied on adult sheep (cf. example 35). In this experiment, the animals were fed a diet of 110 g DCP (Digestible crude protein) per Scandinavian feed unit. The result shows that, with tanning, growth is increased by 19 g per day and protein efficiency by about 20%.

| Effect of tanning of powdered skimmed milk on the growth of kids. | | | |
| --- | --- | --- | --- |
| | Number of animals | Growth g/day | gain % g crude proteine |
| Control | 4 | 117 | 184 |
| Tanned | 4 | 136 | 222 |

EXAMPLE 39

The efficiency of tanning for milk production.

In order to check the efficiency of tanning for milk production, we treated cake with an association of vegetal tannin and formol, in a high moisture medium, followed by drying by the same procedure as described in example 21. The doses of tanning agents and the nature of the cakes are given in the following table.

| Composition of the cake mixture used | | Dose of Tanning Agent p.100 Cake | |
| --- | --- | --- | --- |
| Nature | % | Chestnut Plant Tannin | Formol |
| Groundnut | 50 | 7.5 | 1 |
| Colza | 30 | 6.0 | 0.8 |
| Soya | 20 | 4.5 | 0.6 |

The lactating goats were divided into 3 grousp, whose production was analyzed and recorded for 16 weeks. For the entire duration of the experiment, the control group received a diet supplying the recommended level of protein for this species. In the second group, the amount of crude protein was decreased to 80% of the normal for an 8 week experimental period preceded and followed by a 4 l week control period. In the third group, the animals received this same amount of crude protein (80% of the standard), the supplementary protein necessary to obtain a satisfactory production being provided essentially in the form of tanned cake. It was thus possible to show that reduction of the amount of crude protein level for 8 weeks, between two 4-week control periods resulted in a reduction in the amount of milk ($-5.3\%$) and of nitrogen in the milk ($-4.2\%$) with respect to the estimated yield. In the experimental group, said variation was respectively 0.8% for milk and +5.6% for nitrogen. These last data are similar to those (respectively +1.4 and 7.1%) obtained with the control group (group 1) receiving a normal amount of nitrogen during the whole experiment. Under our experimental conditions, the provision of tanned cake resulted in a more efficient conversion of ingested nitrogen into nitrogen in the milk, for a comparable rate of ingestion.

EXAMPLE 40

Increase in the linoleic acid content of cows' milk

A special concentrate was prepared as follows: 112 kg sunflower seed oil (62% linoleic acid) containing 0.5 g tocopherol per kg oil, was mixed with 750 kg 54% concentrated skim milk and spray dried. During this operation, the protein dries, coating the fine droplets of fat separated by atomization. Half of the powder obtained was pelleted into small cylinders 0.5 cm in diameter and 2 cm in length. The other half was treated as in example 25, but with 20 ml of a commercial formol solution per kg of the mixture to harden the protein covering of the grains of fatty powder and thus to protect the fat from hydrogenation in the rumen.

This spcial formol-treated feed, or the pellets alone, was fed to dairy cows at a rate of 1.2 kg per day for one week, then 2.4 kg for 2 weeks and 1.2 kg for the 4th week.

Results of the analysis of fatty acids in the milk showed that feeding 2.4 kg treated feed with formol under our conditions enabled the linoleic acid in milk fat to be increased for 1.5-2% to 11.5-12% for a daily milk yield of 15 kg.

Tanning treatment applied under these conditions to fat particles coated with protein makes it possible to protect fats from microbial hydrogenation in the rumen.

It is also possible to replace the powdered milk by casein or other protein substances.

According to the invention, the term "short chain aldehyde" includes formaldehyde and the term "low molecular weight aldehyde" refers to $C_1$ 14 $C_7$ aldehydes.

When the term "formol" is used herein, it refers to a commercial standard aqueous solution of formaldehyde obtainable in France consisting of about 30% solution of formaldehyde in water and inhibited by about 8% of methanol.

"Substantially less ammonia" as used herein means a relative decrease due to the tanning treatment of at least 50% in the amount of ammonia released in the artificial rumen test, as described above.

The foregoing examples demonstrated that there is a substantially high correlation between the in vivo and the in vitro data showing the effectiveness of the resistance to deamination of treated nitrogenous animal feeds. The in vitro test is a convenient tool for predicting the efficiency of the tanning treatment, because the artificial rumen used for the in vitro evaluation is inhabited by substantially the same microflora as that appearing in the natural rumen of the fistulated animal.

It is essential to observe that, for a maximum efficiency by the ruminant, nitrogenous animal feeds must meet two requirements, both compulsory:

resist to bacterial deamination in the rumen to be split into their components by protealytic action in the lower parts of the digestive tract of the animal.

Moreover, treated feeds must be non toxic to the host.

In some attempts of the prior art, the conditions of the treatment of nitrogenous animal feeds, the dose and nature of tanning agents are such, that complexes formed between tannin and proteins do not meet all the above mentioned requirements, as shown by in vitro tests in artificial rumen or with proteolytic enzymes.

The invention provides tanned proteinous feeds, which, as proven by all the in vivo examples previously given, meet all the nutritional requisites, because of a judicious choice of tanning substances and processing conditions, specially the relative proportion of tanning substance to protein and the duration of the reaction. Moreover, at any time, the temperature maintained below 80° C. avoids the risks of protein denaturation. So, wholly satisfactory complexes are always obtained under such mild conditions.

The amount of added water to be used in the reaction varies according to the nature of the tanning agent, the nitrogenous feed and the employed device. Generally this amount may vary within the range of 0 to 5 parts by volume per one part by weight of nitrogenous feed. Especially it is possible to carry out the reaction without water except for the water which is naturally present in the reaction components. For example, the formol, which is available on the market in the form of a 30% aqueous formaldehyde solution may be used as tanning agent. In the same way a nitrogenous feed naturally containing from 5 to 15% of water may be used.

It will be pointed out that the above data may vary according to the nature of the used tanning agent and nitrogenous feeds. On the other hand, the content of crude proteins in cakes is very variable according to their origin. As an illustrating example a rapeseed cake contains, by weight, from 30 to 35% of crude protein, while a peanut cake contains from 40 to 55% of crude protein while the corresponding content of a soya cake is from 38 1 to 50%. The isolated proteins of these cakes may contain up to 95% of crude proteins.

Further, the amounts of used tanning agents may vary according to the nature of said agents; for example lower amounts of synthetic tanning agents, such as aldehyde, than the one of tanning agents vegetable origin are used. Moreover, although equivalent results are obtained with short chain aldehydes the amounts of formaldehyde to be used are comparatively lightly lower than in the case of the other aldeydes. When the amount of tanning agents with formaldehyde are expressed as amount of pure formaldehyde, this amount may be up to 0.3% by weight based on the weight of the nitrogenous feed to be treated. Good results are also obtained with amounts of formaldehyde from 0.5 to 1.5%.

We claim:

1. A modified nutritive proteinaceous dry feed for ruminant animals which serves as a digestible source of utilizable nitrogen comprising a complex of a proteinaceous animal feed and a short chain aldehyde, said modified feed being in the form of fine particles to facilitate homogeneous incorporation into other feed mixtures, said complex being relatively stable in respect to bacterial degradation leading to deammination as determined in an artificial rumen, but substantially completely accessible to proteolytic enzymes of the compartments of the animal's alimentary tract which follow the rumen and readily susceptible to enzymatic digestion in vitro by said proteolytic enzymes, the quantity of aldehyde employed in respect to the proteinaceous feed being not in excess of that required to produce resistance to bacterial deammination in the artificial rumen.

2. The modified feed of claim 1, wherein said aldehyde is selected from the group consisting of acetaldehyde, glyoxal and glutaraldehyde.

3. The modified feed of claim 1, wherein the proteinaceous animal feed is casein.

4. The modified feed of claim 1, wherein the proteinaceous animal feed is an oil-seed cake.

5. The modified feed of claim 1, wherein the proteinaceous animal feed is blood meal.

6. The modified feed of claim 1, wherein the proteinaceous animal feed is alfalfa.

7. The process of feeding ruminant animals which comprises feeding such animals the feedstuff of claim 1.

* * * * *

UNITED STATES PATENT AND TRADEMARK OFFICE
CERTIFICATE OF CORRECTION

PATENT NO. : 4,211,795
DATED : July 8, 1980
INVENTOR(S) : LEROY ET AL

It is certified that error appears in the above—identified patent and that said Letters Patent is hereby corrected as shown below:

On The Title Page,

Item [22], please delete "Filed: Dec. 24, 1974" and insert therefor --Filed: Dec. 12, 1974--.

Signed and Sealed this

Fourteenth Day of September 1982

[SEAL]

Attest:

Attesting Officer

GERALD J. MOSSINGHOFF

Commissioner of Patents and Trademarks